United States Patent
Liao et al.

(10) Patent No.: US 11,690,171 B2
(45) Date of Patent: Jun. 27, 2023

(54) CONDUCTIVE BUMP ELECTRODE STRUCTURE

(71) Applicant: SINGULAR WINGS MEDICAL CO., LTD., Zhubei (TW)

(72) Inventors: Chin-Chang Liao, Zhubei (TW); Jheng-Fen Guo, Zhubei (TW)

(73) Assignee: SINGULAR WINGS MEDICAL CO., LTD., Zhubei (TW)

( * ) Notice: Subject to any disclaimer, the term of this patent is extended or adjusted under 35 U.S.C. 154(b) by 121 days.

(21) Appl. No.: 17/242,340

(22) Filed: Apr. 28, 2021

(65) Prior Publication Data

US 2021/0368619 A1  Nov. 25, 2021

(30) Foreign Application Priority Data

May 25, 2020 (TW) .................................. 109117357

(51) Int. Cl.
*H05K 1/02* (2006.01)
*A61B 5/25* (2021.01)
*H05K 1/09* (2006.01)

(52) U.S. Cl.
CPC ............. *H05K 1/0283* (2013.01); *A61B 5/25* (2021.01); *A61B 2562/0209* (2013.01); *H05K 1/09* (2013.01); *H05K 2201/0367* (2013.01); *H05K 2201/10151* (2013.01)

(58) Field of Classification Search
CPC .. H05K 1/0277; H05K 1/0283; H05K 1/0295; H05K 1/11
See application file for complete search history.

(56) References Cited

U.S. PATENT DOCUMENTS

| 9,872,390 B1 * | 1/2018 | Holbery ............... H05K 1/0393 |
| 10,426,029 B1 * | 9/2019 | Glickman .............. H05K 1/118 |
| 2015/0043175 A1 * | 2/2015 | Choi .................... H05K 1/0283 |
| | | 174/254 |

FOREIGN PATENT DOCUMENTS

WO       2014/116825 A1    7/2014

* cited by examiner

*Primary Examiner* — Jeremy C Norris
(74) *Attorney, Agent, or Firm* — Bacon & Thomas, PLLC

(57) ABSTRACT

A conductive bump electrode structure includes a substrate, an elastic circuit layer, at least two conductive bumps, and an insulating layer. The elastic circuit layer is mounted on the substrate, and includes at least one elastic circuit. The at least two conductive bumps are mounted on the elastic circuit layer, and are electrically connected to each other through the at least one elastic circuit. The insulating layer is mounted on the elastic circuit layer, and includes at least two holes. Since there is a gap between the conductive bumps, the conductive bump electrode structure is easy to be bent and fit body curves of various parts of a user. The elastic circuit can stretch or compress along with the user's movement due to its elasticity, thereby increasing suitability of the conductive bump electrode structure to the human body.

14 Claims, 6 Drawing Sheets

CONDUCTIVE BUMP ELECTRODE STRUCTURE

BACKGROUND OF THE INVENTION

1. Field of the Invention

The present invention relates to an electrode structure, and especially relates to a conductive bump electrode structure for sensing physiological signals.

2. Description of the Prior Arts

Previously, most physiological signal sensing devices were combined with medical instruments to detect the patient's physical condition. With the development of electronic devices and sensing technologies, products such as smart bracelets, smart watches, and smart clothes that can sense physiological information of users have been gradually developed. When the physiological signal sensing devices sense the physiological signals of the users, the sensing electrodes of the physiological signal sensing devices need to be contacted to the human body to sense the physiological signals, and the physiological value, such as the user's blood pressure, blood oxygen, heart rate, etc., can be determined according to the physiological signals, so that the user can monitor his own physical state at any time.

Common sensing electrodes for sensing the physiological signals may be metal yarn electrodes or conductive film electrodes. The metal yarn electrode is composed of a conductive cloth knitted by metal yarns. But the metal yarns are prone to fatigue crack and oxidation. The cracked metal yarns may easily penetrate into the stratum corneum of the skin of the user, or may trigger skin irritation when contacting the skin of the user. Further, the cracked metal yarns may generate additional noise to interfere with the sensed physiological signals, and the oxidized metal yarns may shorten the service life of the sensing electrodes. Therefore, the metal yarn electrodes cannot be used for a long time.

The conductive film electrodes are made by printing conductive particles on the film or fabric to sense physiological signals. However, the conductive film electrodes are hard and not flexible. When a size of each of the conductive film electrodes is large, the conductive film electrodes cannot fit the body curves of the user. When each of the conductive film electrodes is small, the conductive film electrodes can easily slip relative to the skin of the user, and the noise may be generated, interfering with the performance of the sensing electrodes.

The metal yarn electrodes and the conductive film metal electrodes both are not flexible. When the user is moving, such as walking, turning, or raising hands, the sensing electrodes are likely unable to adhere to the skin of the user and may fall off from the skin of the user. So the common sensing electrodes must be mounted on the ribs and other parts of the body of the user that are less affected by user's movement to stably sense physiological signals. Therefore, how to make the sensing electrodes fit the user's body curves more easily to fit the user's movement is an important issue.

SUMMARY OF THE INVENTION

To overcome the shortcomings, the present invention provides a conductive bump electrode structure to mitigate or obviate the aforementioned problems. The conductive bump electrode structure includes:

a substrate;

an elastic circuit layer, mounted on the substrate, and having at least one elastic circuit;

at least two conductive bumps, mounted on the elastic circuit layer, and electrically connected to each other through the at least one elastic circuit;

an insulating layer, mounted on the elastic circuit layer, and having at least two holes;

wherein the at least two conductive bumps are each respectively passed through the at least two holes of the insulating layer, and extend out of the insulating layer.

In the conductive bump electrode structure of the present invention, the at least two conductive bumps are in contact with the human body to sense physiological signals of a user. Then the elastic circuit transmits the physiological signals to an external device. The insulating layer is used to prevent the electrical transmission of the at least one elastic circuit from interference of external noise. The at least one elastic circuit is elastic to be stretched with the user's movements, so as to fit the curves of different parts of the human body.

The conductive bump electrode structure of the present invention contacts the human body through the at least two conductive bumps, which reduces the contact area to reduce the discomfort and foreign body sensation. The at least one elastic circuit with elasticity can fit various movements of the user's limbs through stretching or deformation, thereby overcoming the situation that the conventional sensing electrodes are easily damaged by the stretching of the user's limbs. Since there are gaps between the at least two conductive bumps, the conductive bump electrode structure can be bent or folded to fit the curves of the human body, and suitability of the conductive bump electrode structure may not be influenced by its size.

Other objectives, advantages and novel features of the invention will become more apparent from the following detailed description when taken in conjunction with the accompanying drawings.

DETAILED DESCRIPTION OF THE EMBODIMENTS

Figure 1:
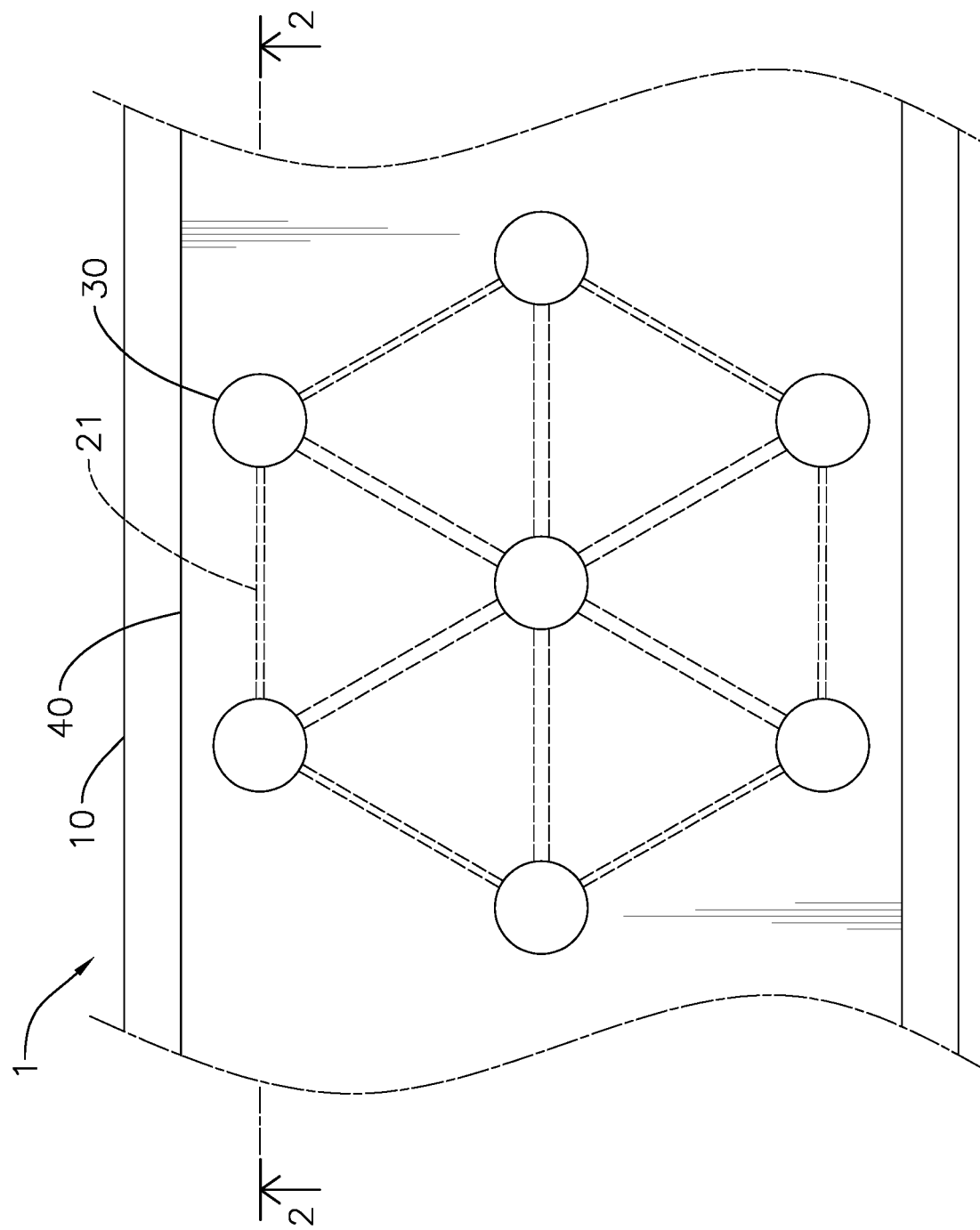
FIG. 1 is a schematic top view of a conductive bump electrode structure of the present invention.
Figure 2:
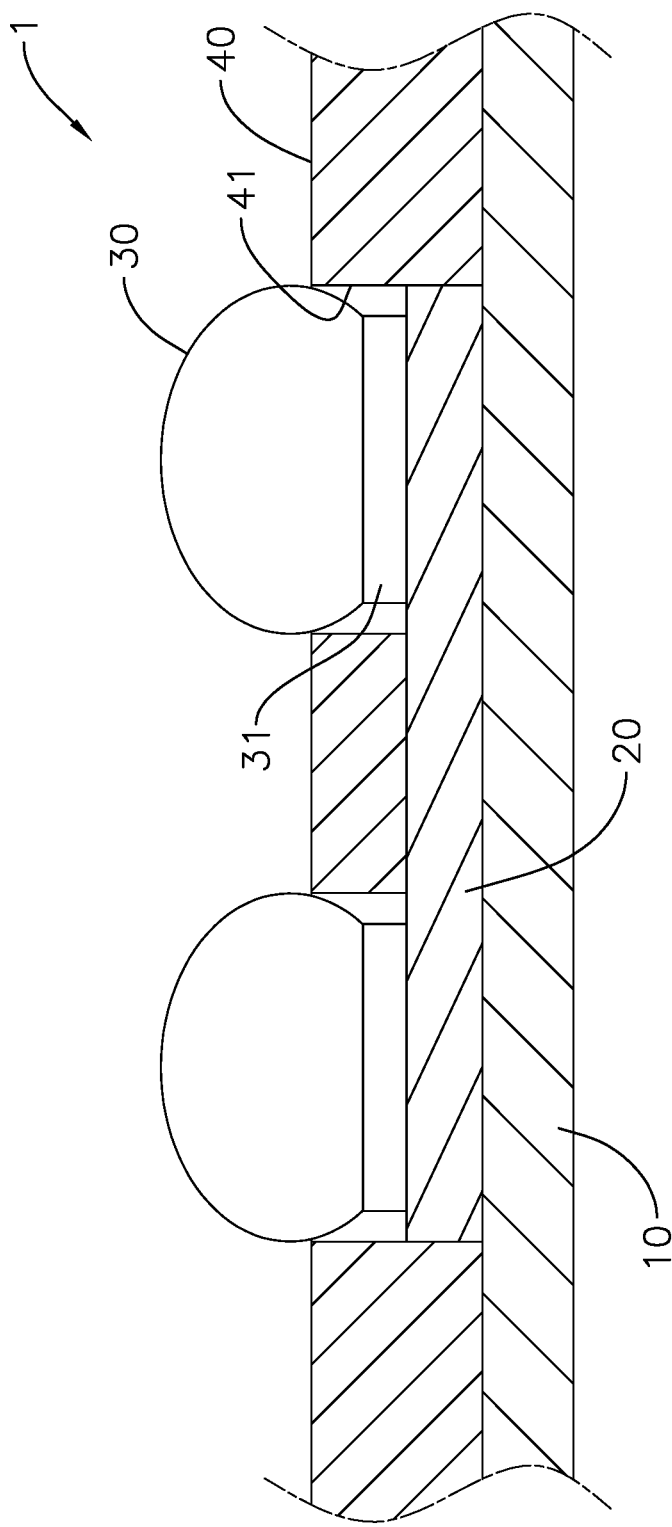
FIG. 2 is a schematic cross-sectional side view of the conductive bump electrode structure of the present invention.

With reference to FIG. 1 and FIG. 2, FIG. 2 is a schematic cross-sectional side view of FIG. 1 across line 2-2. A conductive bump electrode structure 1 of the present invention includes a substrate 10, an elastic circuit layer 20, at least two conductive bumps 30, and an insulating layer 40. The substrate 10 may be a woven product, or may be a cloth, a leather, an elastic film, or an elastic adhesive primer. The elastic film can be further adhered to a steering wheel or a seat armrest, etc., so the conductive bump electrode structure can be applied to various appliances, and thereby the convenience of physiological signal sensing and the application field of the conductive bump electrode structure 1 can be increased.

The elastic circuit layer 20 is mounted on the substrate 10, and includes at least one elastic circuit 21. The at least two conductive bumps 30 are mounted on the elastic circuit layer 20 for sensing physiological signals. Each two conductive bumps 30 are electrically connected to each other through an elastic circuit 21 for transmitting the physiological signals. The at least two conductive bumps 30 can be directly electrically connected to the at least one elastic circuit 21, or can be electrically connected to the at least one elastic circuit 21 through an interface adhesive 31. For example, the at least one elastic circuit 21 may be reformed by a primer, and the at least two conductive bumps 30 can be directly electrically connected to the at least one elastic circuit 21. Thereby the stability of electrical conduction between the at least two conductive bumps 30 and the at least one elastic circuit 21 can be increased. The at least two conductive bumps 30 can be electrically connected to an external electronic device through the at least one elastic circuit 21 to transmit the physiological signals to the external electronic device for subsequent calculation and further application. For example, the at least one elastic circuit 21 may be a straight line circuit, an S-shaped circuit, or a spiral circuit.

The insulating layer 40 and the at least two conductive bumps 30 are both mounted on the elastic circuit layer 20, and the insulating layer 40 has at least two holes 41. The insulating layer 40 covers the elastic circuit layer 20 to prevent the at least one elastic circuit 21 from being short-circuited, or being interfered by noise. The at least two conductive bumps 30 are passed through the at least two holes 41 of the insulating layer 40, and extend out of the insulating layer 40. So the conductive bump electrode structure 1 can measure the physiological signals through the at least two conductive bumps 30 by having the at least two conductive bumps 30 contact the human body.

Referring to FIG. 2, the at least one elastic circuit 21 is a conductive wire made of elastic conductive materials, such as carbon nanotubes, graphene, carbon black, silver, copper, or other conductive material. A length of the at least one elastic circuit 21 is equal to or greater than a distance between the at least two conductive bumps 30. For example, the at least one elastic circuit 21 may be a straight line circuit, so that the length of the at least one elastic circuit 21 is equal to the distance between the at least two conductive bumps 30. When the distance between the at least two conductive bumps 30 increases due to the user's movement, the at least one elastic circuit 21 can be stretched or compressed with the changing distance between the at least two conductive bumps 30 and can fit different body movements due to the deformation of elastic materials.

Figure 3:
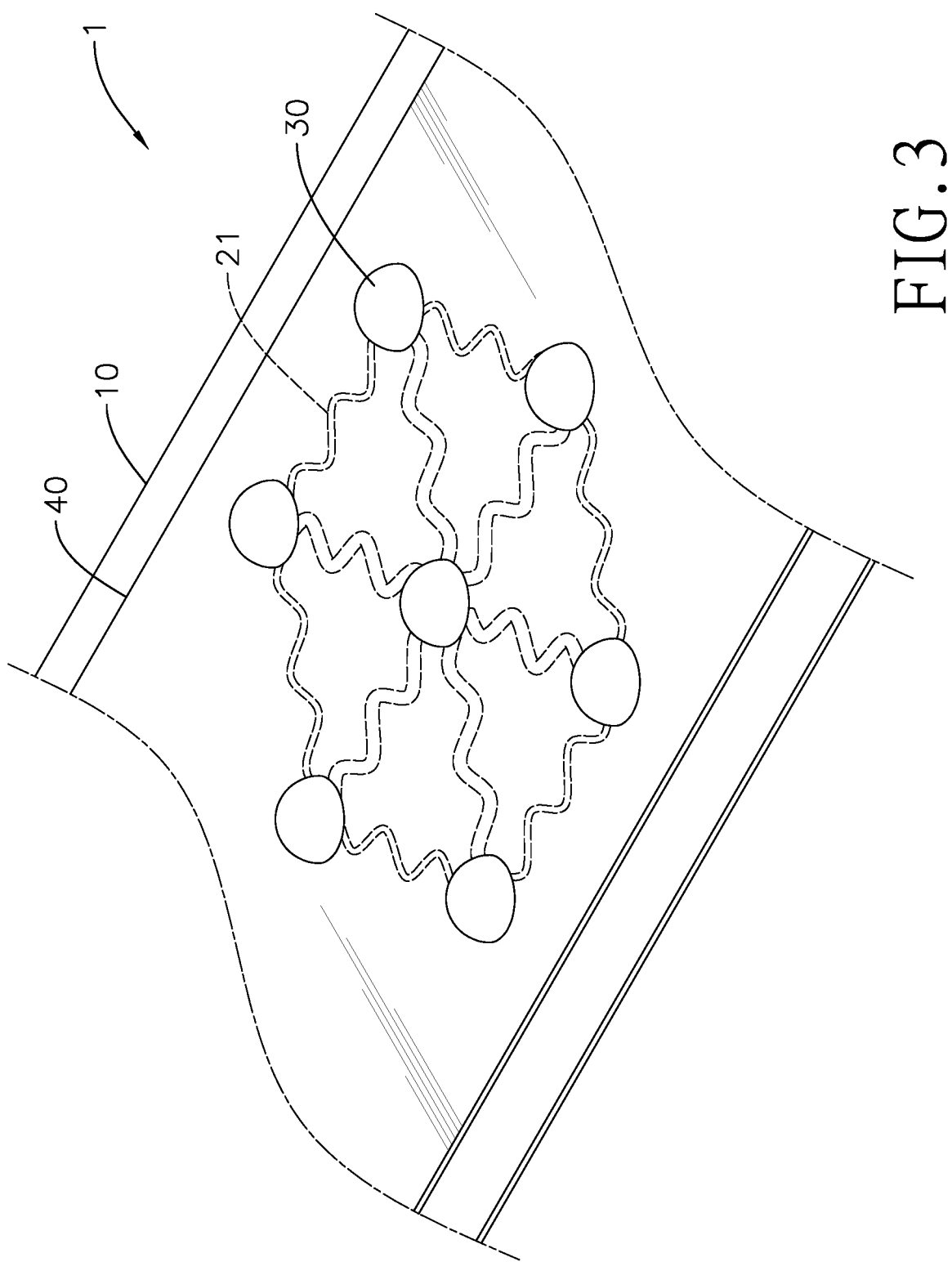
FIG. 3 is a schematic diagram of an embodiment of a conductive bump electrode structure of the present invention.
Figure 4:
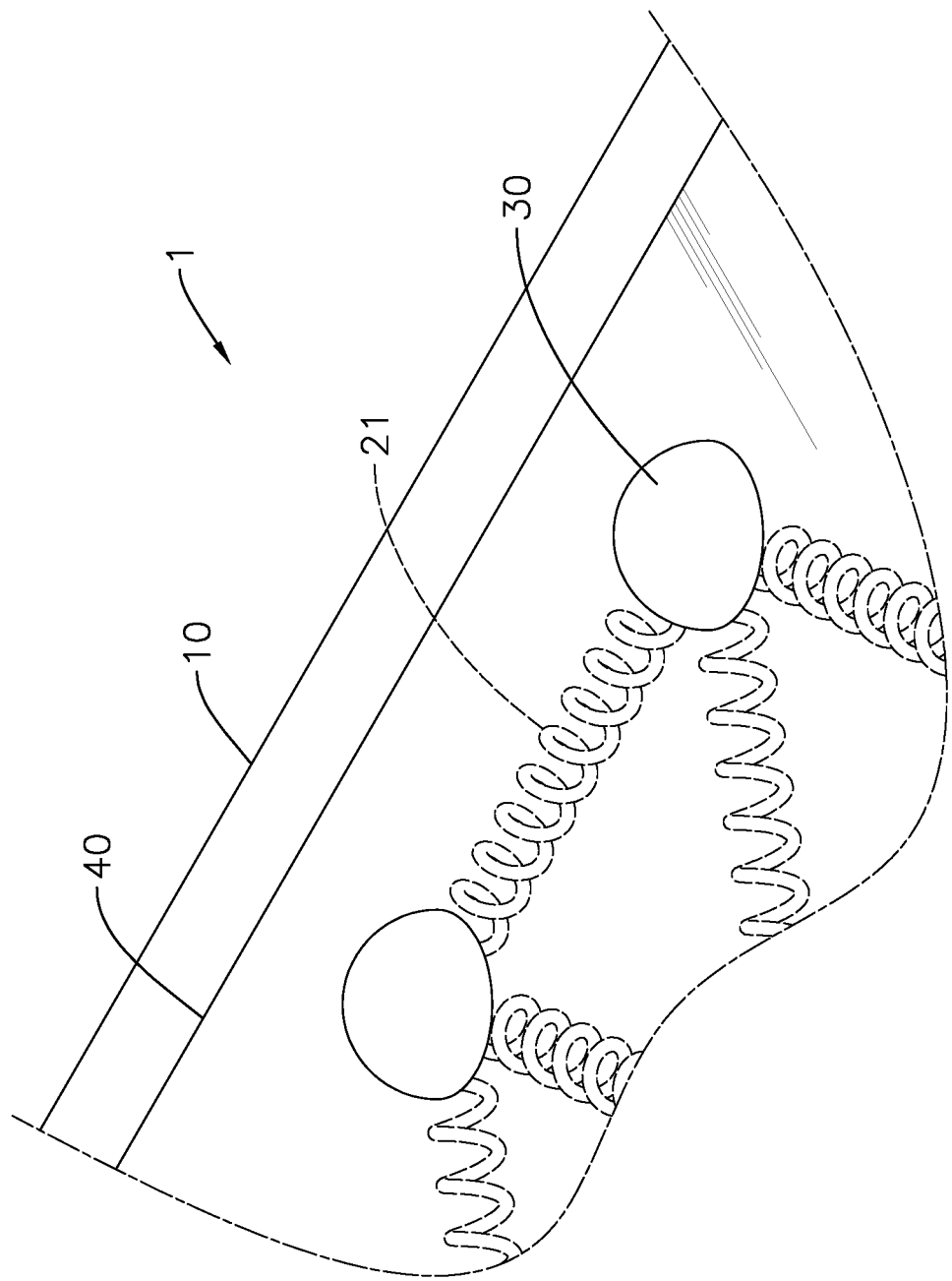
FIG. 4 is a schematic diagram of at least one elastic circuit of the present invention.

Referring to FIG. 3, in one embodiment, the at least one elastic circuit 21 is an S-shaped circuit. Referring to FIG. 4, in another embodiment, the at least one elastic circuit 21 may be a spiral circuit. When the at least one elastic circuit 21 is the S-shaped circuit or the spiral circuit, the total length of the at least one elastic circuit 21 is greater than the distance between the at least two conductive bumps 30. When the at least two conductive bumps 30 contact moving parts of the human body, such as shoulders, elbows, knees, etc., an S-shaped portion or a spiral portion of the at least one elastic circuit 21 can be stretched or compressed with the human's movement. The distance between the at least two conductive bumps 30 can be changed to facilitate the conductive bump electrode structure 1 to fit various body movements when measuring the physiological signals. The at least one elastic circuit 21 is made of conductive materials having elasticity, such as graphene, carbon nanotubes, carbon black, silver, or copper, or other conductive material.

Figure 5:
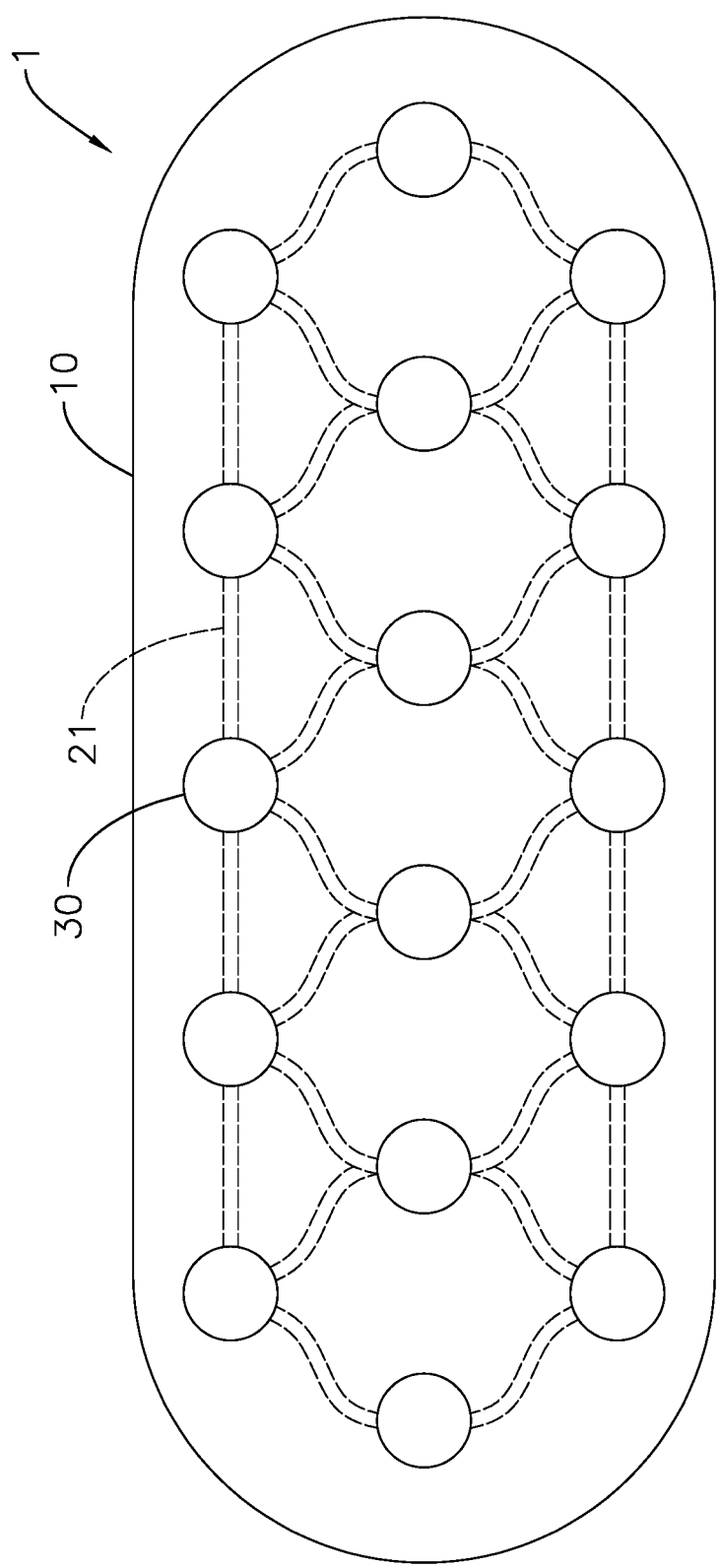
FIG. 5 is a schematic diagram of another embodiment of the conductive bump electrode structure of the present invention.

Referring to FIG. 5, in another embodiment, the elastic circuit layer 20 of the conductive bump electrode structure 1 includes multiple elastic circuits 21. The at least two conductive bumps 30 are multiple, more than two conductive bumps 30. Each two of the conductive bumps 30 are electrically connected to each other by one of the elastic circuits 21 to sense the physiological signals. The conductive bumps 30 on the elastic circuit layer 20 are arranged as a polygonal mesh. In this embodiment, the conductive bumps 30 are arranged as a triangular mesh. Further, the conductive bumps 30 may be arranged as a quadrilateral mesh, a pentagonal mesh, or a hexagonal mesh.

Figure 6:
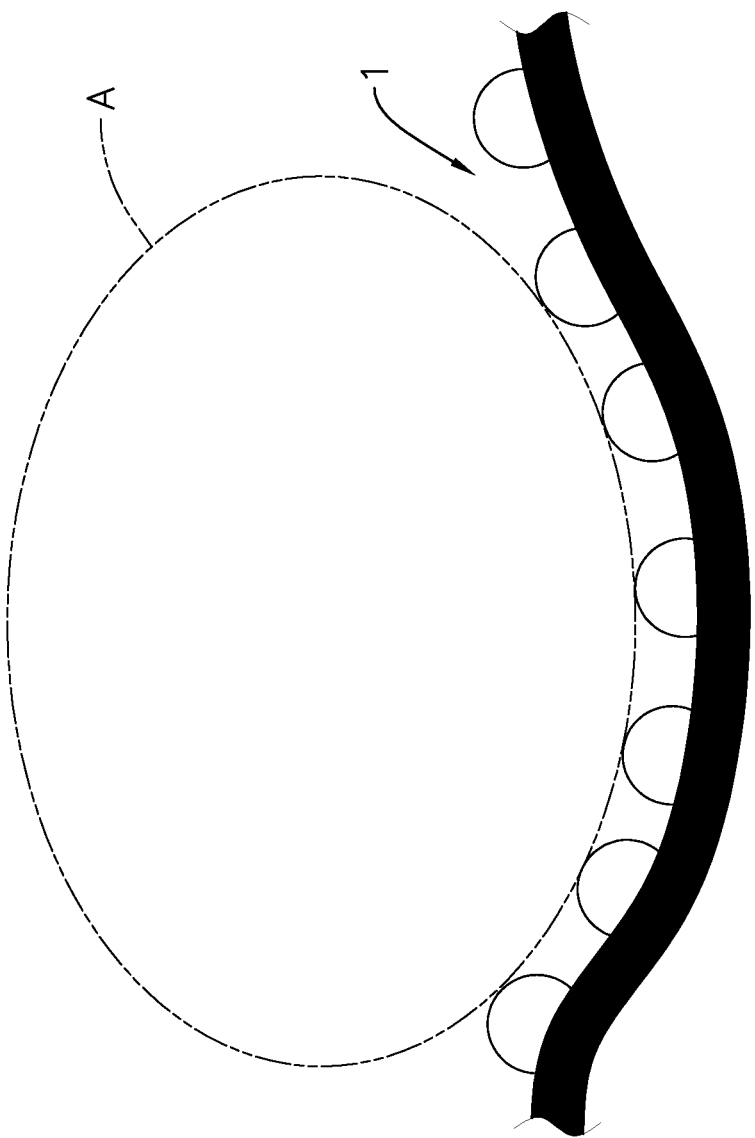
FIG. 6 is a schematic diagram of the conductive bump electrode structure of the present invention in contact with the human body.

FIG. 6 is a schematic diagram of the conductive bump electrode structure 1 contacting an arm A of a human body to measure the physiological signals. In FIG. 6, the arm A is shown in a sectional view. When the conductive bump electrode structure 1 contacts the arm A, an interval between the conductive bumps 30 makes the conductive bump electrode structure 1 easy to bend. The at least one elastic circuit 21 can fit the change of the distance between the conductive bumps 30 by the elasticity of the material or the structure. Therefore, the conductive bump electrode structure 1 can stably fit the arm A to measure the physiological signals, such as blood volume pressure (BVP) signals, electrocardiogram (ECG) signals, respiration signals, electromyography (EMG) signals, or electroencephalography (EOG) signals. Then, blood pressure, blood oxygen concentration, heart rate, body temperature or muscle activity, etc, can be determined according to the physiological signals.

The conductive bump electrode structure 1 of the present invention can be combined with clothing, shoes, gloves and other wearing articles through the substrate 10 to monitor a subject's physiological state at any time, or can be mounted on the objects that the human body frequently contacts, such as seat handles, etc. In this way, the physiological signals measurement can be applied to the daily life, which increases the convenience and the practicality of the physiological signal measurement.

In summary, the conductive bump electrode structure 1 is easy to be bent due to the gap between the conductive bumps 30 of the conductive bump electrode structure 1 of the present invention. The at least one elastic circuit 21 is elastic, so that the conductive bump electrode structure 1 can fit different parts of the human body without being limited by its size. The conductive bump electrode structure 1 can also be mounted on various appliances or devices through the substrate 10 for sensing the physiological signals, and is not limited by the shape of the appliance or device. The conductive bump electrode structure 1 of the present invention contacts the human body only through the at least two conductive bumps 30, which reduces the discomfort of the human body for contacting the conductive bump electrode structure 1. The at least one elastic circuit 21 having the elasticity can be deformed or stretched according to the user's movement. Therefore, the conductive bump electrode structure 1 can adhere the human body well due to the ability to be bent and stretched.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A conductive bump electrode structure comprising:
   a substrate;
   an elastic circuit layer, mounted on an upper surface of the substrate and having at least one elastic circuit;
   at least two conductive bumps, mounted on the elastic circuit layer, and electrically connected to each other through the at least one elastic circuit;
   an insulating layer, mounted on the elastic circuit layer, and having at least two holes;
   wherein the at least two conductive bumps are each respectively passed through the at least two holes of the insulating layer, and extend out of the insulating layer;
   wherein the at least two conductive bumps each respectively have an uppermost end above an uppermost surface of the insulating layer.

2. The conductive bump electrode structure as claimed in claim 1, wherein:
   the at least two conductive bumps are arranged as a polygonal mesh.

3. The conductive bump electrode structure as claimed in claim 2, wherein a length of the at least one elastic circuit is equal to or greater than a distance between the at least two conductive bumps.

4. The conductive bump electrode structure as claimed in claim 2, wherein the at least one elastic circuit is a straight line circuit, an S-shaped circuit, or a spiral circuit.

5. The conductive bump electrode structure as claimed in claim 2, wherein the at least one elastic circuit is made of elastic conductive materials.

6. The conductive bump electrode structure as claimed in claim 2, wherein the substrate is a woven product.

7. The conductive bump electrode structure as claimed in claim 2, wherein the substrate is a cloth, a leather, or an elastic film.

8. The conductive bump electrode structure as claimed in claim 2, wherein the at least two conductive bumps are electrically connected to the at least one elastic circuit through an interface adhesive.

9. The conductive bump electrode structure as claimed in claim 1, wherein a length of the at least one elastic circuit is equal to or greater than a distance between the at least two conductive bumps.

10. The conductive bump electrode structure as claimed in claim 1, wherein the at least one elastic circuit is a straight line circuit, an S-shaped circuit, or a spiral circuit.

11. The conductive bump electrode structure as claimed in claim 1, wherein the at least one elastic circuit is made of elastic conductive materials.

12. The conductive bump electrode structure as claimed in claim 1, wherein the substrate is a woven product.

13. The conductive bump electrode structure as claimed in claim 1, wherein the substrate is a cloth, a leather, an elastic film, or an elastic adhesive primer.

14. The conductive bump electrode structure as claimed in claim 1, wherein the at least two conductive bumps are electrically connected to the at least one elastic circuit through an interface adhesive.

* * * * *